(12) United States Patent
Yuan

(10) Patent No.: US 12,268,949 B2
(45) Date of Patent: Apr. 8, 2025

(54) JOINT PROTECTION DEVICE

(71) Applicant: Hongtao Yuan, Shenzhen (CN)

(72) Inventor: Hongtao Yuan, Shenzhen (CN)

( * ) Notice: Subject to any disclaimer, the term of this patent is extended or adjusted under 35 U.S.C. 154(b) by 1200 days.

(21) Appl. No.: 16/941,771

(22) Filed: Jul. 29, 2020

(65) Prior Publication Data
US 2020/0353343 A1 Nov. 12, 2020

Related U.S. Application Data

(63) Continuation-in-part of application No. 15/328,654, filed as application No. PCT/CN2015/085291 on Jul. 28, 2015, now abandoned.

(30) Foreign Application Priority Data

Jul. 29, 2014 (CN) .......................... 201410365832.3

(51) Int. Cl.
*A61F 5/00* (2006.01)
*A63B 71/12* (2006.01)
*A63B 71/14* (2006.01)

(52) U.S. Cl.
CPC .......... *A63B 71/1225* (2013.01); *A63B 71/14* (2013.01); *A63B 2071/125* (2013.01);
(Continued)

(58) Field of Classification Search
USPC ......................................................... 602/22
See application file for complete search history.

(56) References Cited

U.S. PATENT DOCUMENTS

| 398,892 A | 3/1889 | Golden |
| 674,066 A | 5/1901 | Mitchell |

(Continued)

FOREIGN PATENT DOCUMENTS

| CN | 2162267 Y | 4/1994 |
| CN | 2331389 Y | 8/1999 |

(Continued)

OTHER PUBLICATIONS

International Search Report issued in corresponding PCT Application No. PCT/CN2023/079093, dated Jun. 11, 2023.

(Continued)

*Primary Examiner* — Kim M Lewis
(74) *Attorney, Agent, or Firm* — Westbridge IP LLC

(57) ABSTRACT

Provided is a joint protection device, including a joint protection body whose longitudinal and horizontal shapes match a shape of a joint, joint protection body being an integrally formed rigid hollow housing with an opened bottom and including a front supporting portion and side supporting portions respectively wrapping a front surface and side surfaces of joint to provide front and side support for joint; at least one notch being provided in a portion, close to a joint movement area, of joint protection body, and dividing joint protection body into a plurality of joint pieces; adjacent joint pieces being connected by two local junctions respectively provided at appropriate positions on two sides of joint protection body, and capable of rotating with local junctions as rotation fulcrums; and when joint pieces rotate around rotation fulcrums to a limiting position, adjacent joint pieces coming into contact with each other and stopping rotating.

13 Claims, 19 Drawing Sheets

(52) U.S. Cl.
CPC .............. *A63B 2071/1275* (2013.01); *A63B 2071/1283* (2013.01)

(56) References Cited

U.S. PATENT DOCUMENTS

| | | | |
|---|---|---|---|
| 3,938,207 A | 2/1976 | Drescher | |
| 4,507,804 A * | 4/1985 | Consigny | A41D 13/087 2/21 |
| 4,727,862 A * | 3/1988 | Waddell | A61F 5/0106 602/16 |
| 4,829,988 A * | 5/1989 | Caminiti | A61H 1/008 602/22 |
| 5,152,082 A | 10/1992 | Culpepper | |
| 5,230,699 A * | 7/1993 | Grasinger | A61F 5/05866 128/880 |
| 5,255,391 A | 10/1993 | Levine | |
| 8,516,612 B2 * | 8/2013 | Lynn | A41D 13/087 2/21 |
| 9,802,104 B2 * | 10/2017 | Cox | A63B 71/141 |
| 2005/0054487 A1 | 3/2005 | Rogers | |
| 2005/0251078 A1* | 11/2005 | Fleischmann | A41D 13/087 602/22 |
| 2006/0048259 A1 | 3/2006 | Keppler et al. | |
| 2010/0319217 A1 | 12/2010 | Echols | |
| 2011/0088139 A1 | 4/2011 | Travell | |

FOREIGN PATENT DOCUMENTS

| | | |
|---|---|---|
| CN | 2513403 Y | 10/2002 |
| CN | 1688218 A | 10/2005 |
| CN | 2741614 Y | 11/2005 |
| CN | 1758938 A | 4/2006 |
| CN | 2860158 Y | 1/2007 |
| CN | 201055448 Y | 5/2008 |
| CN | 100420400 C | 9/2008 |
| CN | 101152604 B | 5/2010 |
| CN | 201640642 U | 11/2010 |
| CN | 203235221 U | 10/2013 |
| CN | 104117198 A | 10/2014 |
| CN | 204121708 U | 1/2015 |
| CN | 204618518 U | 9/2015 |
| CN | 204861442 U | 12/2015 |
| CN | 213128287 U | 5/2021 |
| CN | 217337582 U | 9/2022 |
| EP | 0309437 A2 | 3/1989 |
| EP | 2311535 A1 | 4/2011 |

OTHER PUBLICATIONS

European Examination Report in counterpart European Application No. 15827075.1, dated Mar. 27, 2020.
Extended European Search Report in counterpart European Application No. 15827075.1, dated Feb. 16, 2018.
First Office Action in counterpart Chinese Application No. 201410365832.3, dated Apr. 28, 2017.
First Search Report in counterpart Chinese Application No. 201410365832.3, dated Apr. 28, 2017.
International Search Report in corresponding PCT Application No. PCT/CN2015/085291, dated Nov. 3, 2015.
Second Office Action in counterpart Chinese Application No. 201410365832.3, dated Sep. 20, 2017.

* cited by examiner

Section b-b

Section d-d

Section e-e

JOINT PROTECTION DEVICE

CROSS-REFERENCE TO RELATED APPLICATIONS

This application is a continuation-in-part of U.S. patent application Ser. No. 15/328,654, filed on Jan. 24, 2017, which is a national phase of International Application No. PCT/CN2015/085291, filed on Jul. 28, 2015. The International Application claims priority to Chinese Patent Application No. 201410365832.3, filed on Jul. 29, 2014. The afore-mentioned patent applications are hereby incorporated by reference in their entireties.

TECHNICAL FIELD

The present disclosure relates to the technical field of human body movement protection devices, and particular to a joint protection device for an ankle with a footwear.

BACKGROUND

At present, joint protection devices are mainly divided into two types: elastic fiber fabric protection devices with rubber bands and plastic supporting protection devices. Common elastic fiber fabric protection devices with rubber bands include ankle protection devices, wrist protection devices, knee protection devices, waist protection devices, finger protection devices and so on. Their principles are that material elasticity is utilized to increase joint stability so as to buffer and prevent exterior injury and excessive deformation to some extent. However, since the elastic fiber fabric protection devices with rubber bands are simplex in material and structure, so the physical performance in all directions are identical, and thus they are limited in protection of joints under the requirement of consideration to joint movement functions. The reason is very simple: binding strength needs to be enhanced to increase protection to joints, which may have a negative effect on joint movement; instead, protection to the joints may be reduced if the binding strength is reduced to take the joint movement into account. Common plastic supporting protection devices include knee protection devices in skating and skiing sports, and finger joint supporting protection devices in football goalkeeper gloves. This type of protection devices makes up for some deficiencies of the former type of protection devices. However, at present, this type of protection devices is larger in structural volume, unsuited to bodies, uncomfortable for wearing, complex in structure, and thus relatively high in cost.

To a basketball fan, finger injury is not fatal as knee injury or ankle injury. However, fingers are slender and vulnerable, unable to bear great strength, and are in contact with a basketball momently. Therefore, fingers are more susceptible to get injured. Once the fingers are injured, a seriously negative effect may be undoubtedly caused on the basketball sport. Injured fingers may be more vulnerable, and thus may be easily susceptible to repeated injury, which causes the injured fingers hardly be restored for a long time. In the field of basketball sports, a basketball finger protection device that can provide effective protection to fingers has been always expected to appear. However, at present, there is only one type of finger protection device in the market, namely, an elastic barrel-shaped finger protection device with a rubber band. However, this type of finger protection device is not comfortable and is limited in protection of fingers. Therefore, it is still a problem to be solved in the art to develop a finger protection device that can provide effective protection to fingers and is comfortable.

In addition to fingers, the protection of other body parts such as ankles, knees, etc. also faces the above problems. Besides, for the joint movement protection, in addition to the front support, the lateral support is also important. Therefore, there is a need for a structure capable of supporting and protecting a joint in all directions.

Chinese patent CN2741614Y and U.S. Pat. No. 4,727,862A both disclose structures that can provide front support to joints. However, since the joint protection body of these structures is solid and is placed on the joint rather than wrapping around the joint, these structures are bulky and inflexible and thereby affect the joint movement (such as dribbling and throwing by hand) and wearing (for example, the joint protection body at the ankle is too thick to be worn in a shoe). Moreover, they cannot provide the lateral support to joints.

Besides, the joint protection device may also be combined with other relevant products to realize some additional functions. One of the important applications is to combine a joint protection body with a footwear to protect the ankle from being injured. Chinese patent CN100420400C discloses a shoe with a protector (i.e. an ankle protector), which, however, does not have a good protective effect and flexibility. Moreover, this kind of shoe is complex in structure and expensive in cost, and the protector part of the shoe is exposed outside the shoe. Thus, this kind of shoe can be regarded as a simple combination of the protector and the shoe, and hence the appearance of the shoe is greatly limited. U.S. Pat. No. 5,152,082A discloses a shoe that has a supporting and protecting function and a certain flexibility. However, since its supporting member is divided into a plurality of strip-shaped structures, and the upper part of the strip-shaped structures (which plays a key role in protecting the ankle) is disconnected and cannot not well wrap the ankle and its above parts, thus the supporting and protecting performance is very limited. In addition, the plurality of supporting strips (of which the upper part is disconnected) will affect the function of the cushion material (usually a sponge) in the shoe. For example, the sponge will be caught into the gap between adjacent supporting strips, and the sponge will be punctured at the disconnected places.

Therefore, there is a need for a joint protection device that is capable of supporting a joint in all directions without affecting normal joint movements, and is capable of being combined with other relevant products as a whole, such as being combined with a footwear as a whole to play a role of ankle protection.

SUMMARY

An object of the present disclosure lies in overcoming the above deficiencies and providing a joint movement protection device that is light and thin in volume, is simple in structure, can be firmly attached to a joint part without affecting normal joint movements, and is low in cost.

The joint protection device provided by the present disclosure comprises a joint protection body whose longitudinal and horizontal shapes match a shape of a joint, the joint protection body being an integrally formed rigid hollow housing with an opened bottom and comprising a front supporting portion and side supporting portions distributed on two sides of the front supporting portion, the front supporting portion and the side supporting portions respectively wrapping a front surface and side surfaces of the joint to provide front and side support for the joint; at least one notch being provided in a portion, close to a joint movement area, of the joint protection body, the at least one notch dividing the joint protection body into a plurality of joint pieces, adjacent joint pieces being connected by two local junctions respectively provided at appropriate positions on two sides of the joint protection body, the adjacent joint pieces being capable of rotating with the local junctions as rotation fulcrums; and when the joint pieces rotate around the rotation fulcrums to a limiting position, the adjacent joint pieces coming into contact with each other and stopping rotating.

The joint protection device can have a fixing device that fixes the joint protection body to a wearer's joint. For example, the fixing device can be integrally formed onto the joint protection device, or a fabric can be sewed to the joint protection device by sewing. Meanwhile, the joint protection device may not have a fixing device but is fixed by means of other separate fixing devices such as adhesive tapes, or by combination with other devices, in particular but not limited to wearable devices, such as footwear.

Optionally, edges of the upper notch or the lower notch and the joint pieces are rounded off.

Optionally, a bottom width of the upper notch is larger than a top width of the upper notch.

Optionally, heights of a plurality of the joint pieces increase or decrease in a step-wise manner, and each joint piece extends outwardly and covers a top of the upper notch.

Optionally, the joint protection device includes a strip-shaped fixing belt, one end of the fixing belt is integrally formed on one side of the joint protection body while the other end of the fixing belt is provided with at least one buckle, the joint protection body is provided with through holes matched with the buckle, and the fixing belt, after wrapping around the joint, is fastened to the through hole by means of the buckle; wherein the other end of the fixing belt is further provided with at least one saw-toothed barb, and the joint protection body is further provided with corresponding through holes or semi-through holes matched with the saw-toothed barb.

Optionally, the joint protection device comprises an opened fixing ring or a closed fixing ring which are fixed to the joint protection body, and the opened fixing ring or the closed fixing ring is formed integrally with the joint protection body.

Optionally, an elastomer with a good elasticity is injected between the joint pieces through overmolding, to support a part of a body weight by an elasticity of the elastomer when the joint projection body is bent.

Optionally, at least one joint piece is further provided with hook-shaped structures matched with each other, and when the joint is bent inwardly until the hook-shaped structures contact with each other, the joint stops bending; wherein the joint protection body is further provided with a notch, a middle part of the notch is provided with a junction, and the joint pieces on two sides of the junction rotate in any direction with the junction as a rotation fulcrum.

Optionally, one end of the joint protection body extends to form a thin wall having an L-shape in a cross section.

Optionally, the joint protection device further comprises a footwear, the joint protection body is provided within the footwear, the footwear comprises a shoe sole, an upper and a heelpiece, and the joint protection body is disposed at the heelpiece.

Optionally, heights of the adjacent joint pieces increase or decrease in a step-wise manner; the joint protection body is placed laterally of, behind, and medially of a heel of the wearer's foot, and in a state in which a leg is upright, a longitudinal axis (X1) of the joint protection body is consistent with a longitudinal axis (X2) of the heelpiece; a lower part of the joint protection body is fixed to the heelpiece, and an area, corresponding to the rear of the heel, of the joint protection body is not fixed to the heelpiece; a cushion structure is provided between the joint protection body and the wearer's foot; a contour of a bottom edge of the joint protection body is designed to be consistent with a contour of the shoe sole at its bottom edge, but gradually expands laterally in an upward direction; and a fastener of the footwear fits and fixes the joint protection body to the wearer's leg and foot.

Optionally, an end, close to a foot sole, of the joint protection body extends in a lateral direction of the heelpiece, and is completely opened along a direction of the shoe sole; or the end, close to a foot sole, of the joint protection body opens in the direction of the shoe sole, while a bottom edge of the joint protection body has a fixing structure that fixes the joint protection body to the shoe sole; wherein the joint protection body is placed and fixed between inner and outer layers of the upper; the inner and outer layers of front and rear areas, corresponding to an ankle, of a collar of the footwear are elastic in a direction from the heel to the leg.

Optionally, the cushion structure between the joint protection body and the wearer's foot is used by one of the following: adhering a molded foam member to the joint protection main body; or directly molding a foam material onto the joint protection body by using a mold.

Optionally, a hardness of the foam member is between 13 HC and 30 HC.

Optionally, a ratio G:F of a minimum thickness G to a length F of the local junction is between 0.15 and 1.1; and an included angle formed between the notch and a horizontal direction is within ±35°.

The joint protection device proposed in the embodiments of the present disclosure does not affect normal joint movement in use, thereby effectively protecting human joints. In addition, it is simple in structure, light and thin, and low in cost, and can be worn and removed conveniently and quickly.

DESCRIPTION OF EMBODIMENTS

Figure 1:
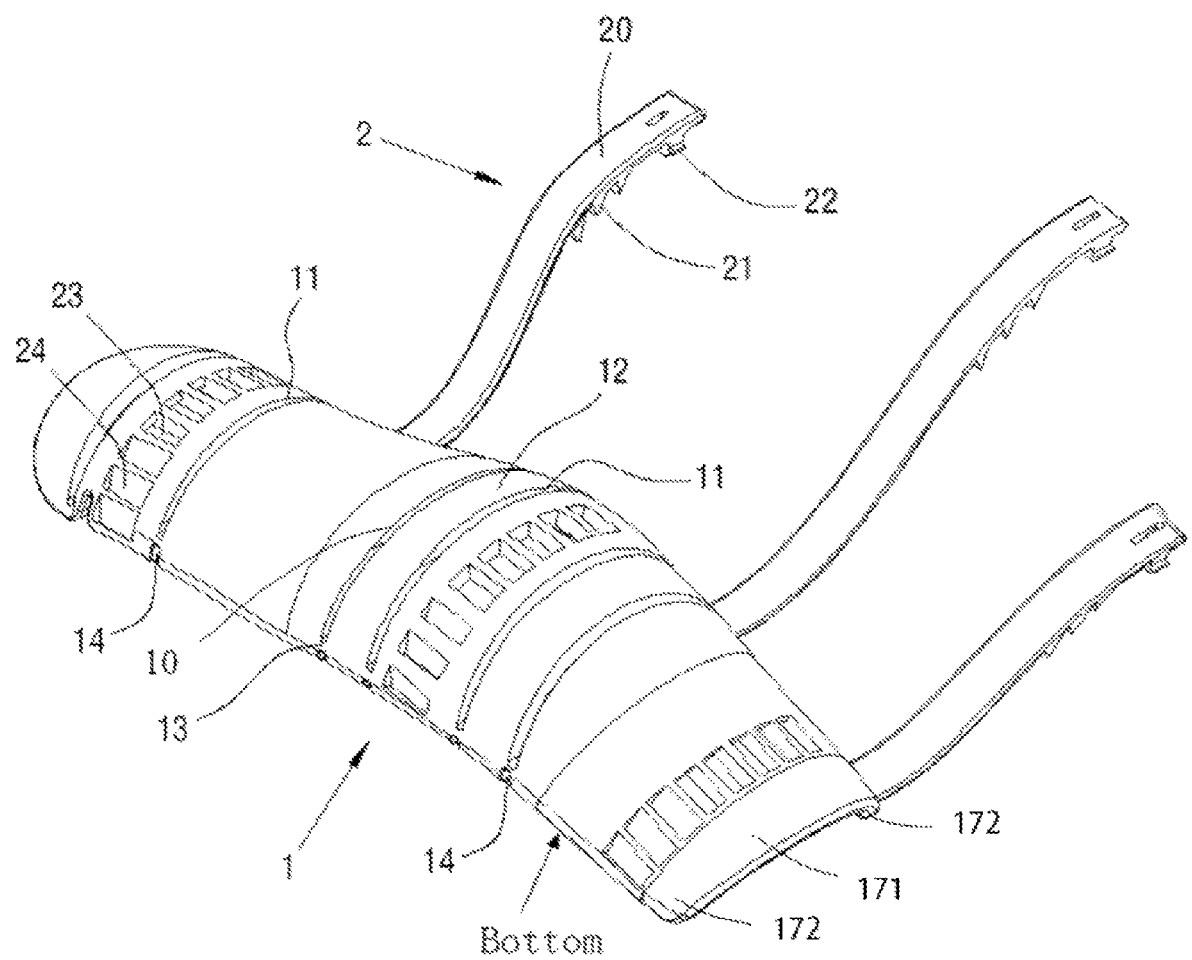
FIG. 1 is a front perspective view of a joint protection device according to an embodiment of the present disclosure.
Figure 2:
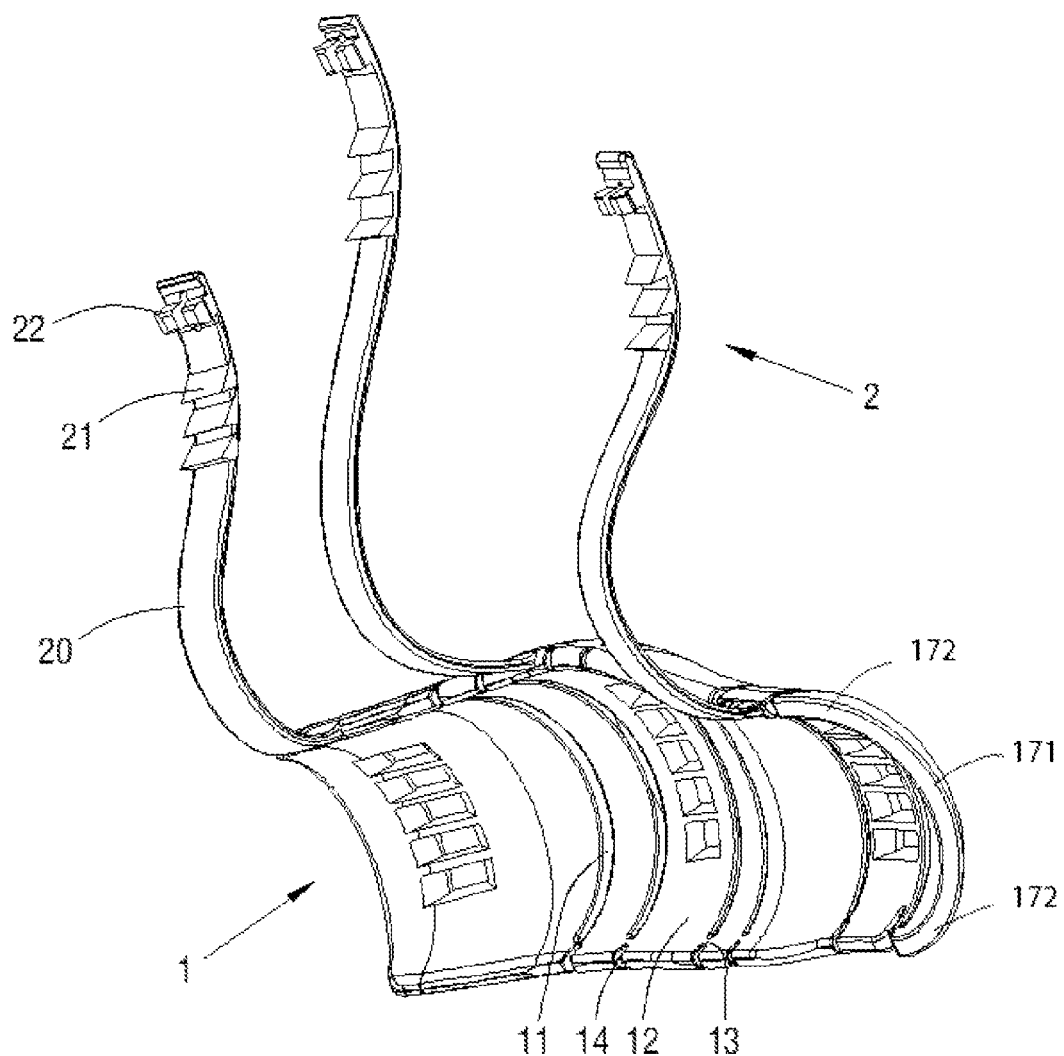
FIG. 2 is a side perspective view of the joint protection device according to an embodiment of the present disclosure.
Figure 3:
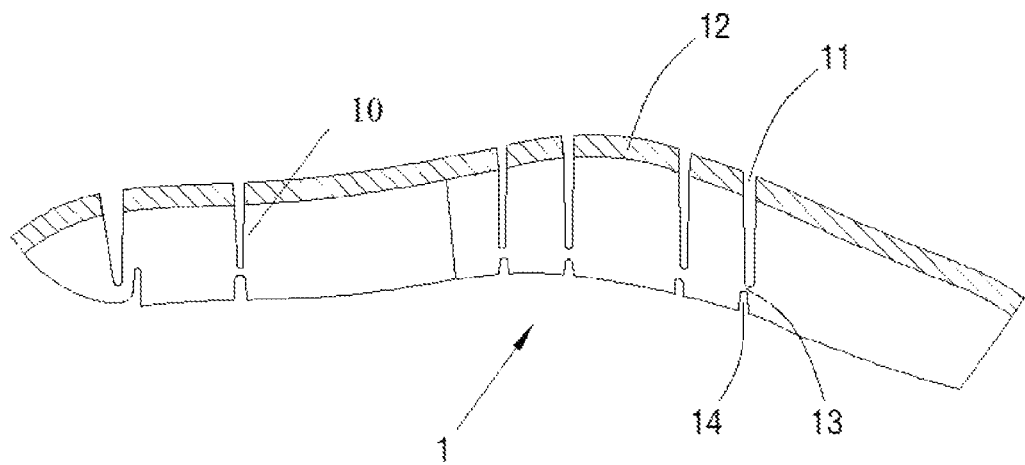
FIG. 3 is a schematic diagram of a longitudinal cross-sectional view of the joint protection device according to an embodiment of the present disclosure.
Figure 4:
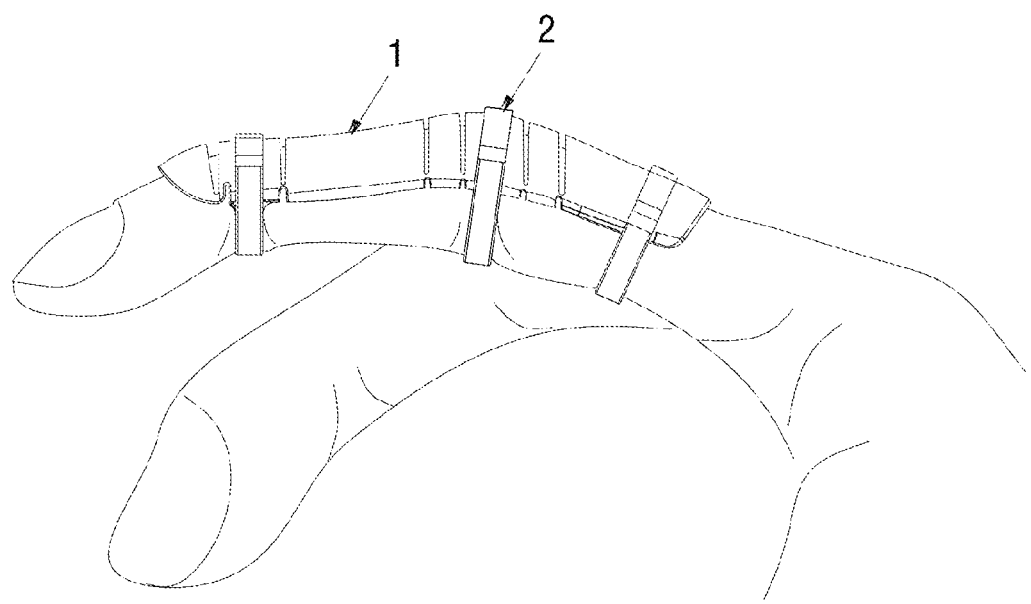
FIG. 4 is a diagram of a use state of the joint protection device according to an embodiment of the present disclosure.
Figure 5:
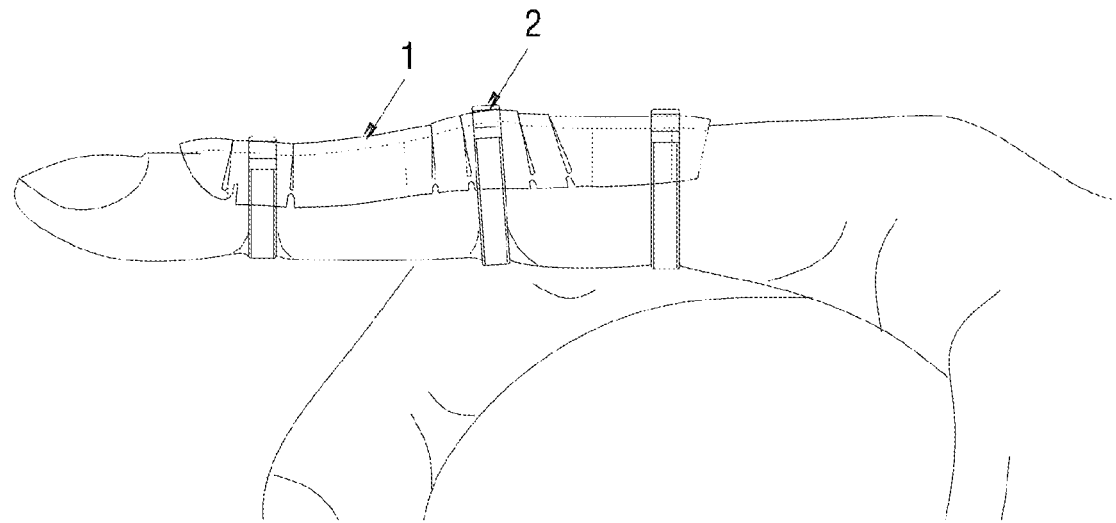
FIG. 5 is a diagram of a use state of the joint protection device according to an embodiment of the present disclosure.

In order to make the aims, technical solutions and advantages of the present invention clear, the technical solution of the present disclosure is described in detail in the following with reference to specific embodiments and drawings of specification. It is understood that the following specific embodiments are merely illustrative and not for limiting.

The implementations of the present disclosure are described in detail in the following with reference to specific embodiments.

As shown in FIG. 1 to FIG. 34, embodiments of the present disclosure provide a joint protection device, including a joint protection body 1 whose longitudinal and horizontal shapes match a shape of a joint. The joint protection body is an integrally formed rigid hollow housing with an opened bottom and include a front supporting portion 171 and side supporting portions 172 distributed on two sides of the front supporting portion 171. The front supporting portion 171 and the side supporting portions 172 respectively wrap a front surface and side surfaces of the joint to provide front and side support for the joint. At least one notch 10 is provided in a portion, close to a joint movement area, of the joint protection body 1. At least one notch 10 divides the joint protection body 1 into a plurality of joint pieces 12. Adjacent joint pieces 12 are connected by two local junctions 13 respectively provided at appropriate positions on two sides of the joint protection body 1. The adjacent joint pieces 12 are capable of rotating with the local junctions 13 as rotation fulcrums. When the joint pieces 12 rotate around the rotation fulcrums to a limiting position, the adjacent joint pieces 12 contact with each other and stop rotating.

When the local junction 13 is located at a bottom edge of the joint protection body 1, the joint protection body 1 only has an upper notch 11; when the local junction 13 is located at a certain distance above the bottom edge of the joint protection body 1, the joint protection body 1 has both an upper notch 11 and a lower notch 14. Taking the finger supporting protector as an example, when the fingers are straightened, adjacent joint pieces 12 on both sides of each upper notch 10 contact with each other and do not rotate any longer. In this way, the joint is prevented from overbending toward a direction to back of a hand, thereby achieving the aim of protecting a finger. Regarding to finger joints, most importantly, the finger needs to be prevented from overbending toward the back of the finger, which is a primary cause to injury to the finger joints. The case of the above embodiment may be adopted when restricting the finger joints from bending toward a direction of a palm of the hand is left out of account.

In an embodiment of the present disclosure, the adjacent joint pieces of the upper notch 11 just come into contact with each other when the joint is straightened, at the moment the adjacent joint pieces 12 do not rotate anymore because of a rigid support action of the joint protection body, so that the joint is prevented from overbending toward the direction of the back of the hand, thereby achieving the aim of protecting the finger. When the joint bends toward the direction of the palm of the hand to a certain extent, two adjacent joint pieces 12 of the lower notch 14 just come into contact with each other, at the moment the adjacent joint pieces 12 of the lower notch 14 do not rotate anymore because of a rigid support action of the joint protection body, so that the joint is prevented from overbending toward the direction of the palm of the hand, thereby achieving the aim of protecting the finger.

In an embodiment of the present disclosure, edges of the upper notch 11 or the lower notch 14 and the joint piece 12 are rounded off. Here, edges of the upper notch 11 or the lower notch 14 and the joint piece 12 are rounded off to improve fitness to the human body and performance.

Figure 10:
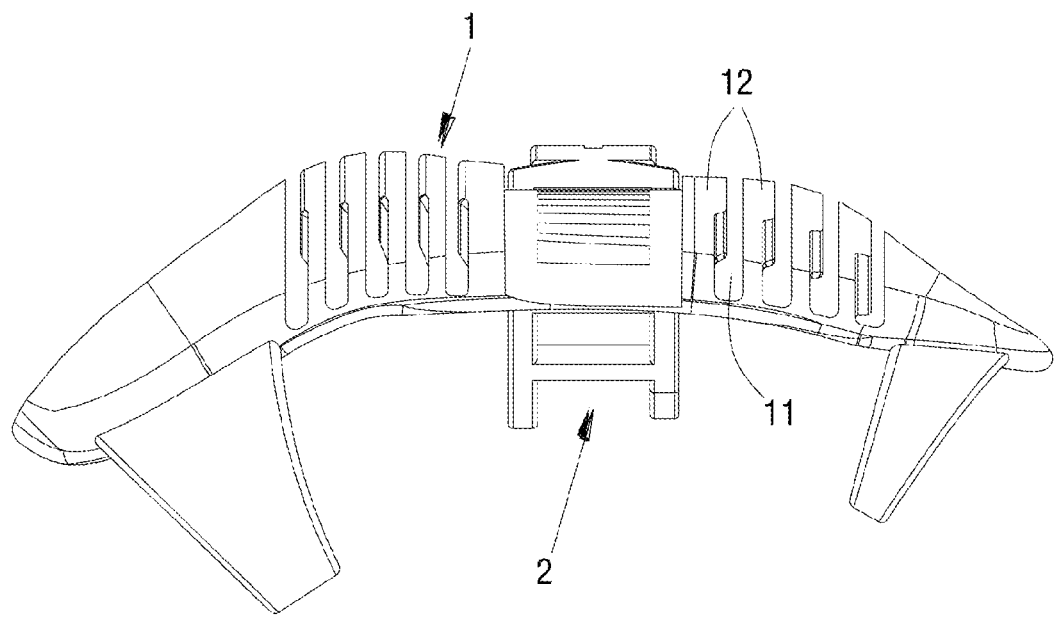
FIG. 10 is a side view of a joint protection device according to another embodiment of the present disclosure.

In another embodiment of the present disclosure, as shown in FIG. 10, bottom width of the upper notch 11 is larger than top width thereof, so that rotating part connecting the adjacent two joint pieces 12 is stronger and not easy to break, thus the overall elasticity of the joint protection device is improved. Of course, according to actual demands, in other embodiment, it is possible to take some other means to improve the overall elasticity of the joint protection device.

Figure 12:
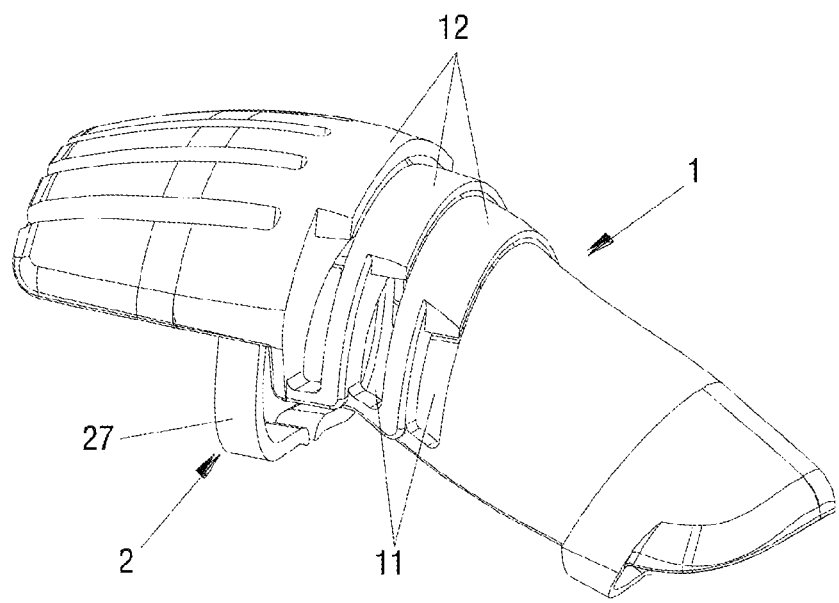
FIG. 12 is a side perspective view of a joint protection device according to another embodiment of the present disclosure.

In an embodiment of the present disclosure, as shown in FIG. 12, heights of a plurality of the joint pieces 12 increase progressively, and each joint piece 12 extends outwardly and covers over top of the upper notch 11, thus, when finger joints are bend to some extent in a direction towards palm, the adjacent two joint pieces 12 rotate reversely around the rotation fulcrum 13, then, top of the upper notch 11 opens, since edge of each joint piece 12 extends outwards and cover over top of the upper notch 11, top of the upper notch 11 will not expose entirely, preventing injury from external objects to fingers or invasion of external objects, thus the overall safety of the joint protection device is improved.

In an embodiment of the present disclosure, as shown in FIG. 1 to FIG. 12, the above joint protection device includes at least one fixing device 2, such as strip-shaped fixing belts 20. An end of the fixing belt 20 and a side of the joint protection body 1 are integrally molded, and another end of the fixing belt 20 is provided with at least one buckle 22, correspondingly, the joint protection body 1 is provided with a plurality of through holes 23 matched with the buckle 22. In this way, the fixing belt 20, after wrapping around the joint, is fastened to the through hole 23 on the joint protection body 1 by means of the buckle 22, so that the fixing belt 20 can form a connection with the joint protection body 1, and therefore the joint protection body 1 is tightly fixed over the joint.

Meanwhile, another end of the fixing belt 20 may be further provided with at least one saw-toothed barb 21, correspondingly, the above joint protection body 1 is further provided with through holes 23 or semi-through holes 24 matched with the saw-toothed barb 21, so that the saw-toothed barb 21 is engaged with the through hole 23 or semi-through hole 24.

Figure 6:
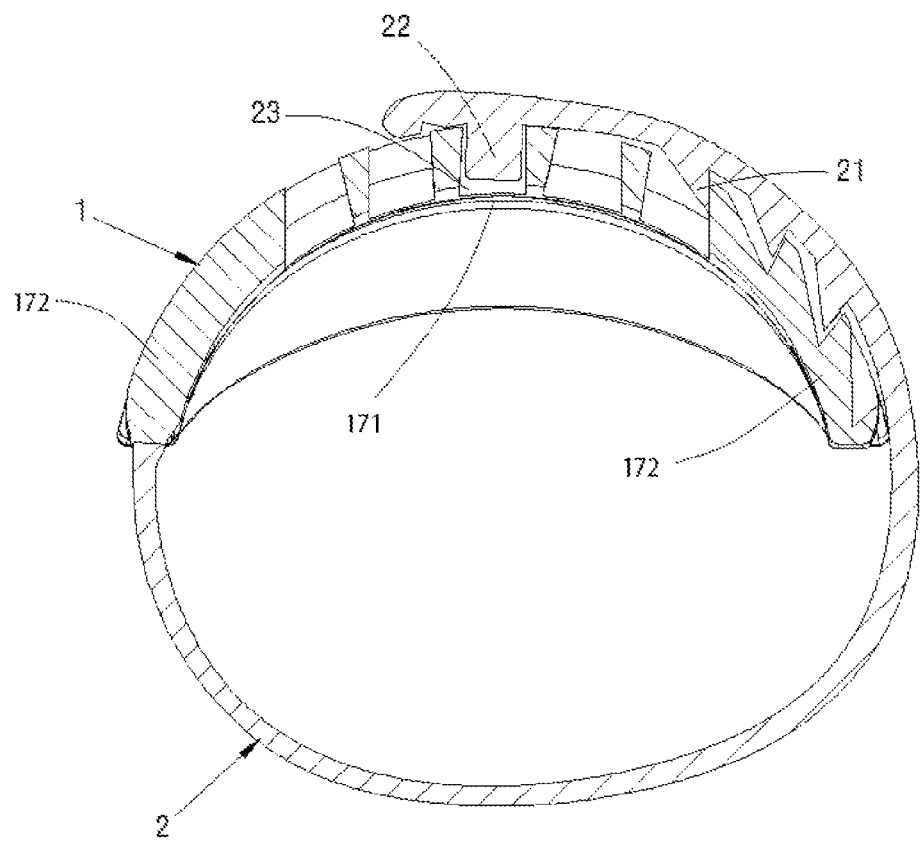
FIG. 6 is a schematic diagram of a lateral cross-sectional view of a fastened fixing belt of the joint protection device according to an embodiment of the present disclosure.
Figure 7:
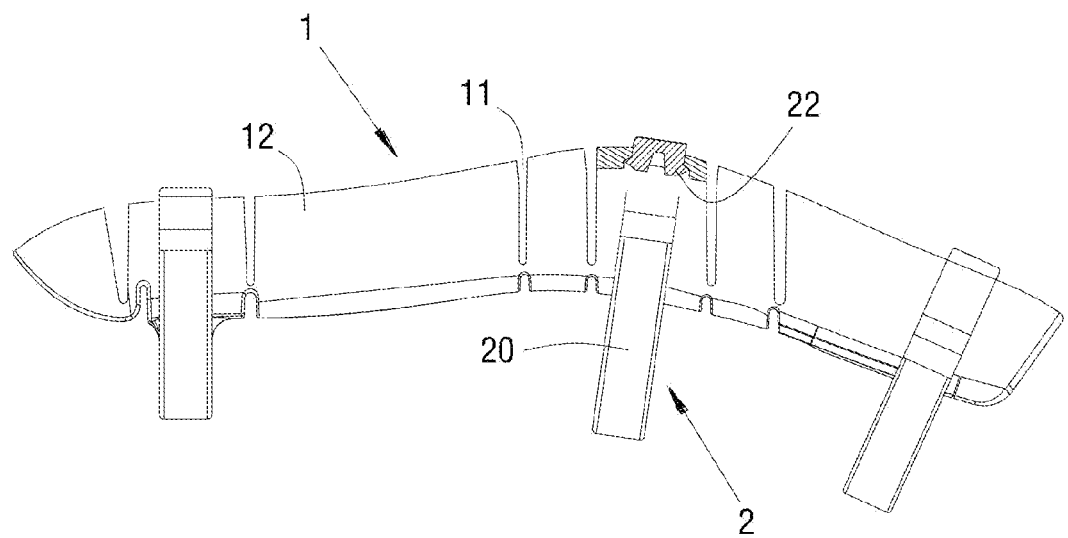
FIG. 7 is a side view of the joint protection device according to an embodiment of the present disclosure.
Figure 8:
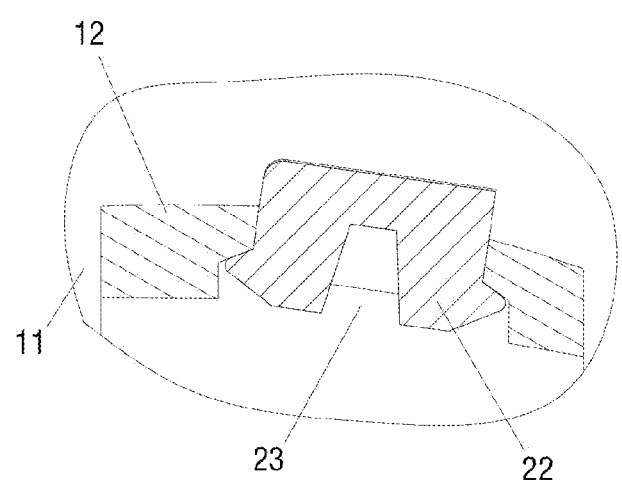
FIG. 8 is a partial sectional view of the joint protection device according to an embodiment of the present disclosure.

FIGS. 6-8 display a detailed state when the buckle 22 is fastened to the through hole 23. The saw-toothed barb 21 and the buckle 22 cooperate with different through holes 23 or semi-through holes 24 so that a degree of tightness of the fixing belt 20 can be adjusted. In this way, the same joint protection body can fit to fingers of different sizes to a certain extent. The above saw-toothed barb 21 is mainly responsible for bearing a longitudinal pulling force on the fixing belt 20, and the buckle 22 is mainly responsible for fitting the fixing belt 20 to the joint protection body 1 to ensure a good engagement between the saw-toothed barb 21 and the through hole 23 or semi-through hole 24. The combined use of the saw-toothed barb 21 and the buckle 22 enables the joint protection body 1 to be stably and reliably fixed on the joint, and be worn and removed conveniently and quickly.

In other embodiments of the present disclosure, a suitable structural style adopting other types may be selected as required for the fixing device 2. For example, a traditional Velcro® tape can be adopted for fixation, or the joint protection body 1 may be inlaid and fixed into a glove or an elastic fabric. Alternatively, the joint protection device itself may not include a fixing device 2, but is fixed by means of a separate fixing belt of other types. For example, a separate adhesive tape may be adopted to wrap it around and fix it to the wearer's body. An independent fixing belt, which can adopt a material in a proper form and match with a buckle having a proper structure to closely fitting the joint protection body 1 to the joint of the human body. It should be noted that the term "closely fitting" used in the context of this text refers to a positional relationship between the joint protection body and the joint. It is not limited to directly fitting the joint protection body to the joint. On the contrary, the joint protection body may also be indirectly fitted to the joint. For example, the situations in which a certain structure (such as a fabric) exists between the joint protection body and the joint also belong to the "closely fitting" situations. In addition, the term "joint" used in the context of this text does not exactly correspond to the "joint" in anatomy, but refers to an area where the joint is located or even includes areas near it. For simplicity, only "joint" is used for the description.

Figure 9:
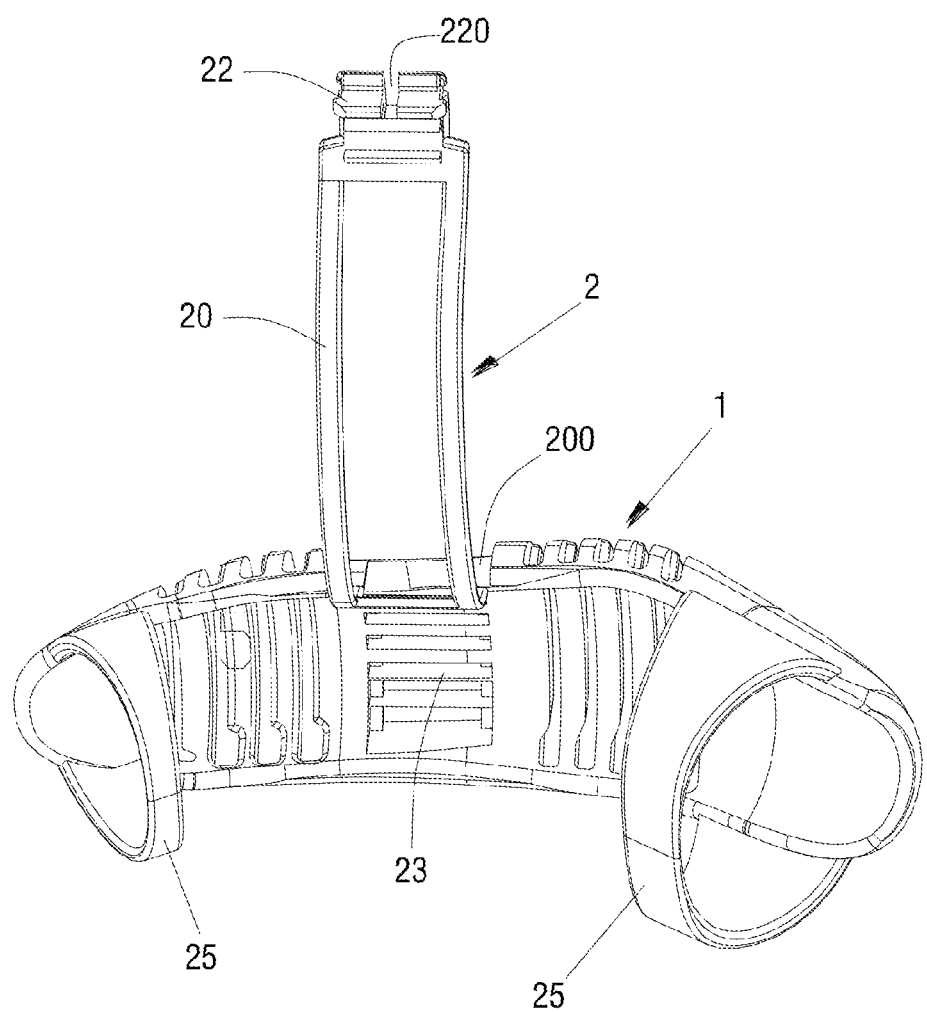
FIG. 9 is a side perspective view of a joint protection device according to another embodiment of the present disclosure.

As shown in FIG. 9, in another embodiment of the present disclosure, the above fixing device 2 may include the above fixing belt 20 and a fixing ring 25 arranged on two ends of the joint protection body 1. The fixing ring 25 adopts a soft plastic annular structure. At the same time, the joint protection body 1 is provided with a containing slot 200 on the back, to accommodate the fixing belt 20, i.e. when the fixing belt 20 surrounds the back of the joint protection body 1, the outer end portion of the fixing belt 20 is accommodated in the containing slot 200, so that the height of the fixing belt 20 is flush with the back of the joint protection body 1, avoiding being unaesthetic and scratch; furthermore, an opening 220 is provided at the middle of the buckle 22, thanks to the opening 220, the buckle 22 can access to the above through hole 23 more easily, improving convenience to take on and off.

Figure 11:
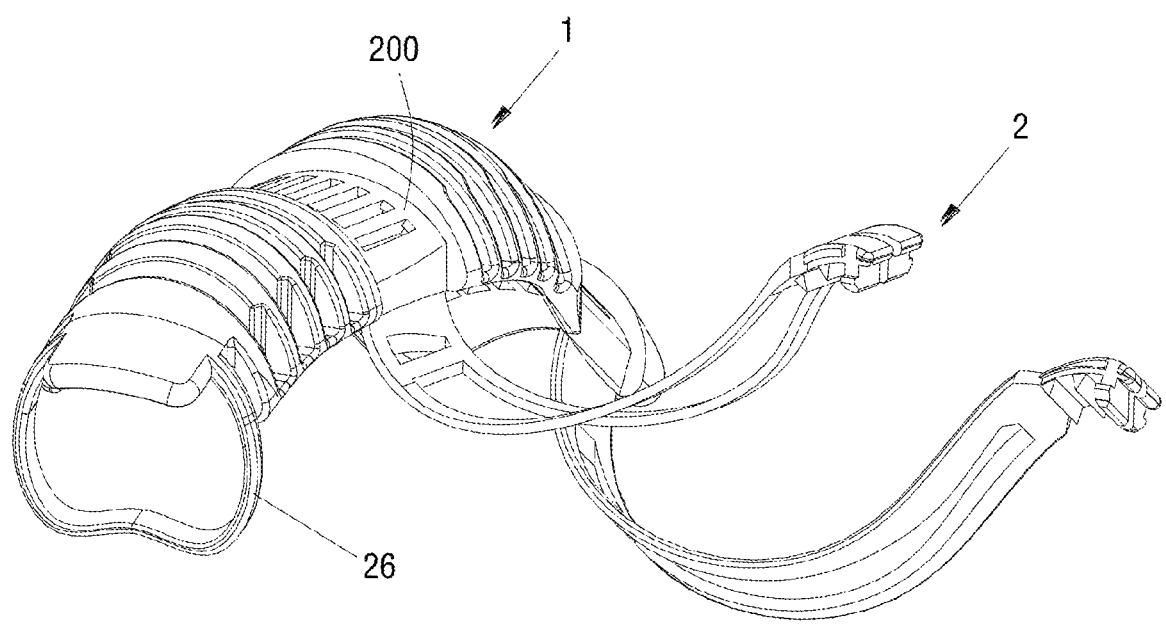
FIG. 11 is a front perspective view of a joint protection device according to another embodiment of the present disclosure.

Alternatively, as shown in FIG. 11, the fixing device 2 may also include a closed fixing ring 26 which is fixed to the joint protection body 1. Here, the closed fixing ring 26 is set to be corrugation, so that it can adapt to the joint having different sizes, broadening the application of the joint movement protection device and meeting people's different demands. At the same time, the joint protection body 1 is also provided with a containing slot 200 on the back, to accommodate the fixing belt 20, thereby avoiding being unaesthetic and scratch.

Alternatively, as shown in FIG. 12, the fixing device 2 may also include an opened fixing ring 27 which is fixed to the joint protection body 1. As such, it can adapt to the joint having different sizes, broadening the application of the joint protection device and meeting people's different demands.

Alternatively, the joint protection body 1 can be fixed on joint by the following means: the joint protection body 1 matched with the shape and structure of joint to be protected may be inlaid or fixed into a fabric, and then the fabric is wrapped around the joint and fixed by Velcro®.

Figure 13:
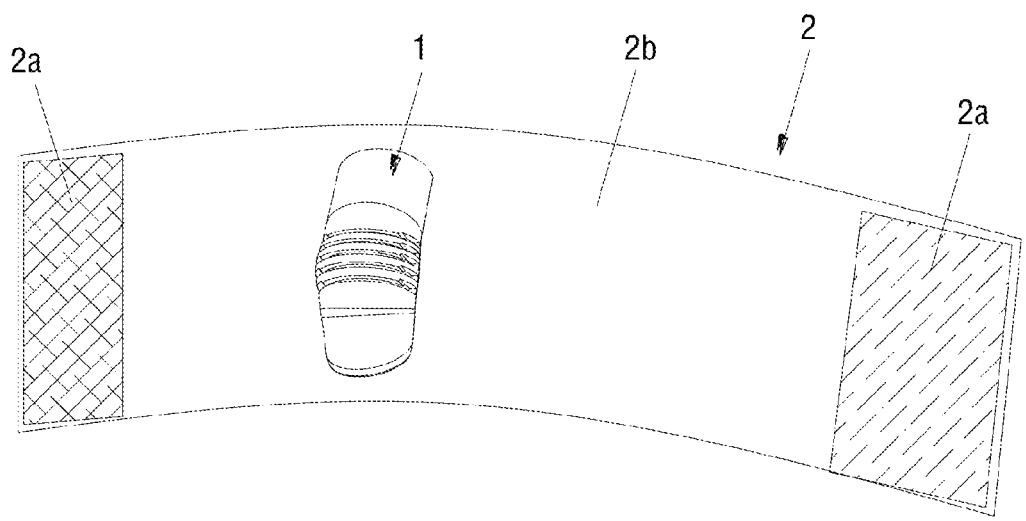
FIG. 13 is a front perspective view of a joint protection device according to another embodiment of the present disclosure.

FIGS. 13, 17 to 19 are examples of an application of a protector in which the joint protection body is connected to the fabric. Specifically, as shown in FIG. 13, for example, in order to protect knee-joint, the fixing device 2 includes Velcro® 2a and fabric 2b, and the joint protection body 1 is disposed on fabric 2b, then the fabric 2b is wrapped around the leg, and at last, Velcro® 2a' on two ends of the fabric 2b', are adhered or engaged together.

Figure 17:
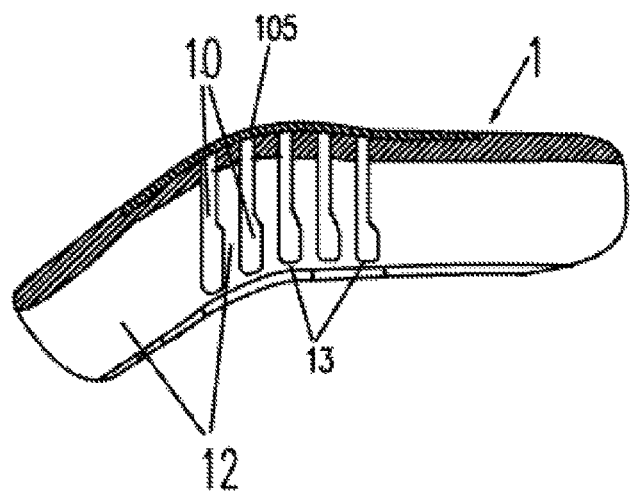
FIG. 17 is a structural diagram of a joint protection body with a weight-bearing elastomer according to an embodiment of the present disclosure.

Exemplarily, as shown in FIG. 17, on the joint protection body 1, the elastomer 105 may be injected between the joint pieces 12 by using overmolding or similar processes. The selected elastomer 105 is a material with a good elasticity, such as TPU, silicone, etc. When the human body squats and the knees bend, the gap between adjacent joint pieces 12 becomes larger. At this point, the joint pieces 12 will be pulled backward due to the elasticity of the elastomer 105 between the joint pieces 12, thereby a supporting force for the knee is generated by the joint protection body 1, and in this way the effect of sharing the body weight borne by the knee joint can be further improved.

Figure 18:
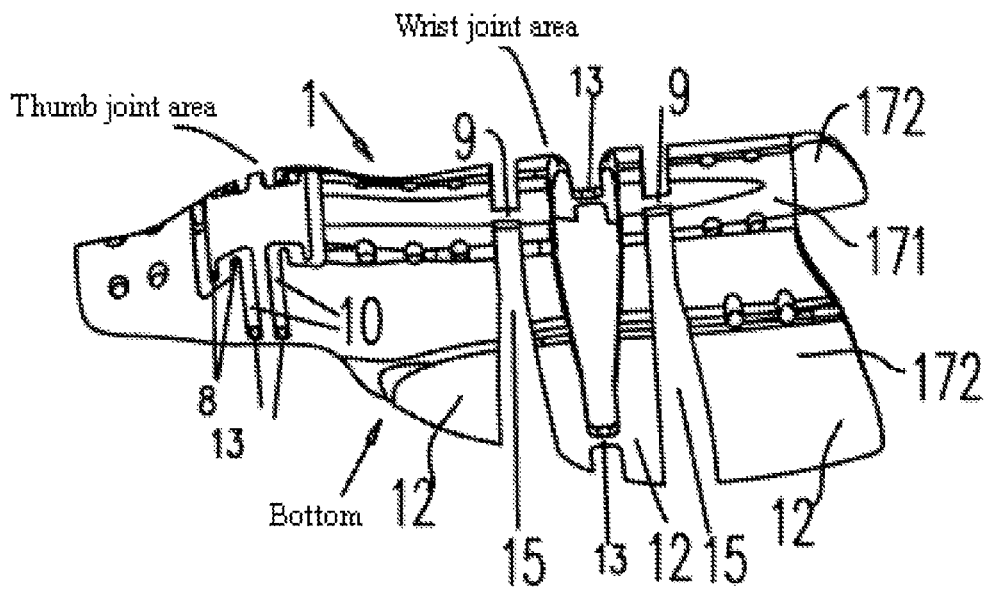
FIG. 18 is a structural diagram of a joint protection body for protecting a wrist and a thumb according to the present disclosure.

FIG. 18 is a joint protection body 1 which can be applied to a joint protection device for a wrist and a thumb. At least one notch 10 is provided in each of the portions, close to a wrist joint movement area and a thumb joint movement area, of the joint protection body 1. The notch 10 divides the joint protection body 1 into a plurality of joint pieces 12. Adjacent joint pieces 12 are connected by two local junctions 13 respectively provided at appropriate positions on two sides of the joint protection body 1. Adjacent joint pieces 12 are capable of rotating with the local junctions 13 as rotation fulcrums. The joint pieces 12 of the joint protection body 1 in the thumb joint area are also provided with hook-shaped structures 8 matched with each other. When the joint (for example, the thumb) is bent inwardly until the hook-shaped structures 8 contact each other, the joint stops bending. In this way, the joint protection body 1 can protect the thumb joint no matter when it is bent inward or outward. The joint protection body 1 is also provided with a notch 15 in the wrist joint area, and a junction 9 is provided in the middle of the notch 15. The joint pieces 12 on two sides of the junction 9 can rotate in any direction with the junction 9 as a rotation fulcrum, so as to satisfy the movement requirements of the wrist joint in all directions. Meanwhile, the movement range of the wrist joint is limited to a certain extent due to contact of adjacent joint pieces, thereby achieving the purpose of protecting the wrist joint.

Figure 19:
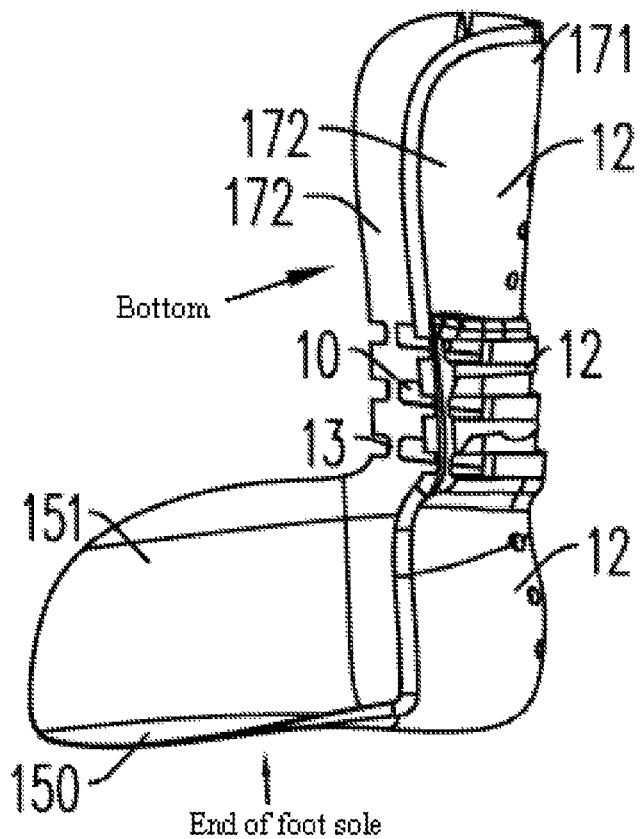
FIG. 19 is a structural diagram of a joint protection body for protecting an ankle according to the present disclosure.

FIG. 19 is a joint protection body 1 which can be applied for an ankle. FIG. 19 shows a left view of the joint protection body 1. In the area of ankle and the area around the ankle, the longitudinal and transverse shapes of the joint protection body 1 are consistent with the shape of the wearer's foot. The joint protection body 1 is an integrally formed rigid hollow housing with an opened bottom, and is provided with at least one notch 10 in an area close to the ankle. The notch 10 divides the joint protection body 1 into a plurality of joint pieces 12. Adjacent joint pieces 12 are connected by two local junctions 13 respectively provided at appropriate positions on two sides of the joint protection body 1, and are capable of rotating with the local junctions 13 as rotation fulcrums. The heights of the plurality of joint pieces 12 increase or decrease in a step-wise manner. The joint protection body 1 includes a front supporting portion and side supporting portions respectively distributed on two sides of the front supporting portion. The front and side supporting portions can wrap around the front and sides of the joint to provide front and side support for the joint. One end of the joint protection body 1 extends to form a thin wall having an L-shape in a vertical cross section. To be specific, the joint protection body 1 extends on an end close to the foot sole to form a foot sole supporting member 150 that has the same shape and size as the wearer's foot sole, and is provided with a side plate 151 on the inside of the wearer's foot. The foot sole supporting member 150 and the side plate 151 connect with each other and form a thin wall having an L-shape in a vertical cross section for strengthening the lateral fixation to the foot.

Figure 14:
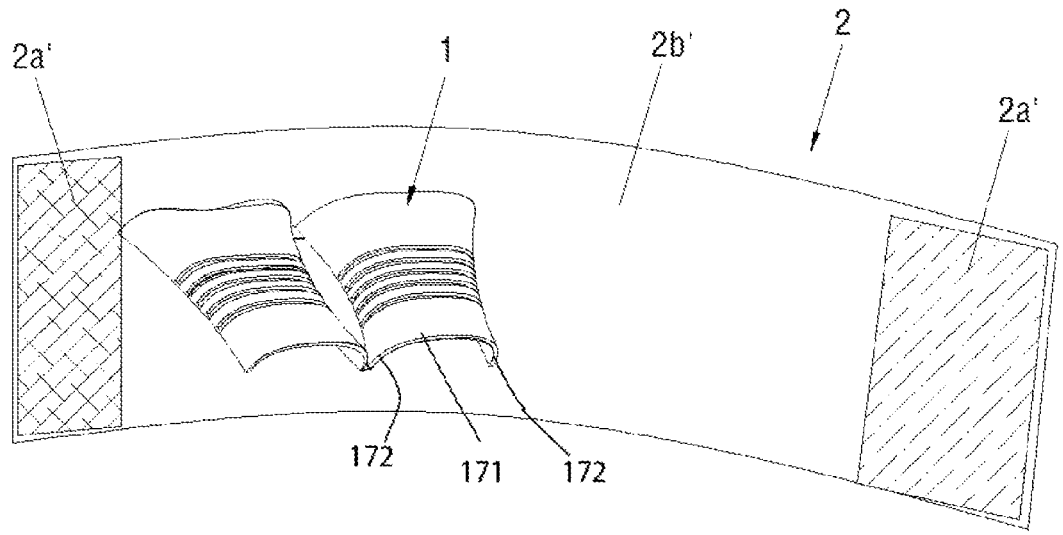
FIG. 14 is a front perspective view of a joint protection device according to another embodiment of the present disclosure.
Figure 15:
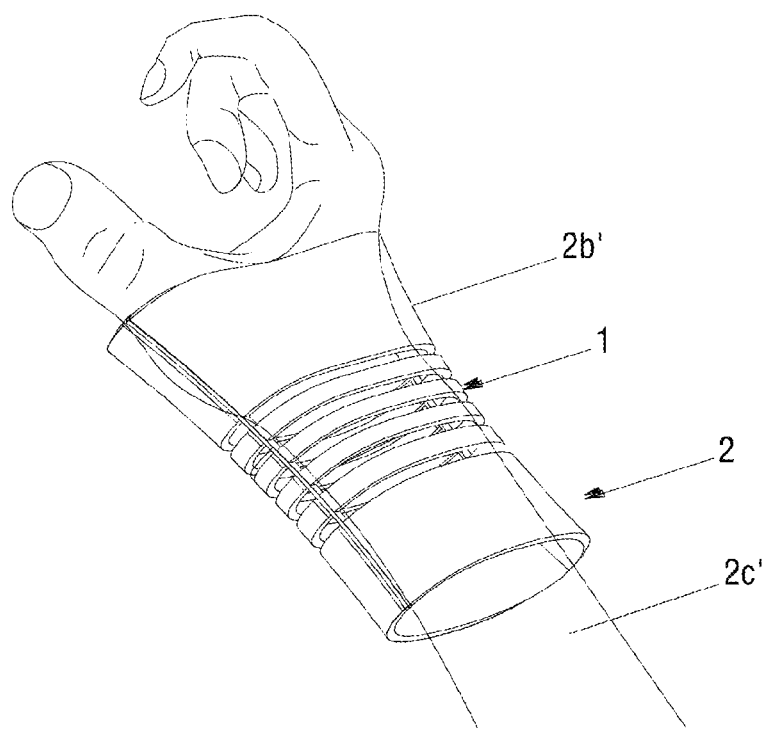
FIG. 15 is a diagram of a use of a joint protection device according to another embodiment of the present disclosure.
Figure 16:
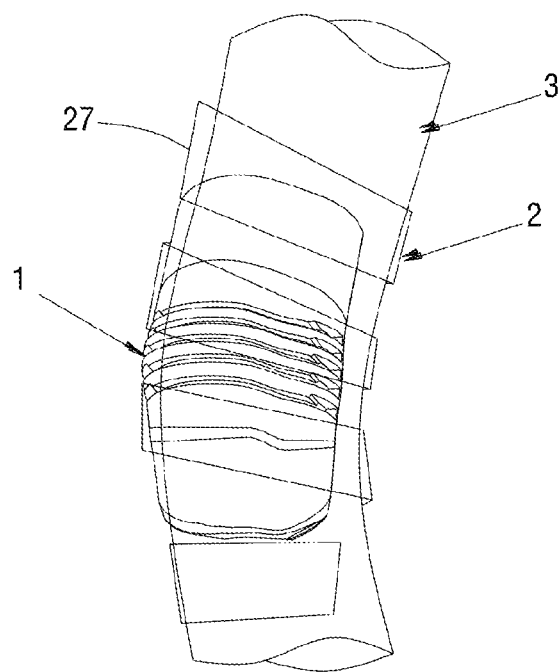
FIG. 16 is a diagram of a use of a joint protection device according to another embodiment of the present disclosure.

Furthermore, if people need to restrict movement of joint in multiple directions, a plurality of joint protection bodies 1 can be used, i.e. the joint protection body 1 matched with the shape and structure of joint to be protected may be inlaid or fixed into a fabric with certain shape and size, and then the fabric is wrapped around the joint and fixed by Velcro®. Specifically, as shown in FIGS. 14-15, for example, in order to protect wrist joint, the fixing device 2 includes Velcro® 2a' and fabric 2b', and two joint protection bodies 1 are disposed on fabric 2b', when in use, the two joint protection bodies 1 are positioned on the wrist joint of an arm 2c' oppositely, then the fabric 2b' wraps around the arm 2c', and at last, Velcro® 2a' on two ends of the fabric 2b' are adhered or engaged.

The joint protection device according to the present disclosure can be further applied to some other parts of human body, such as elbow, ankle, waist, wherein the structures and principles thereof are the same, but different shapes should be designed for different body parts to be protected.

Alternatively, the above joint protection device can be used in combination with self-adhesive non-woven fabrics or various tape or gummed paper or some other fixing means, directly applied to sports protection or health care. For example, in order to protect knee-joint, see FIG. 16, the fixing device 2 includes self-adhesive non-woven fabric 27 (or tape or gummed paper), and the joint protection body 1 is positioned tightly on knee-joint 3, then joint protection body 1 is fixed on the knee-joint 3 through self-adhesive non-woven fabric.

In other embodiments of the present disclosure, the above joint protection device can also be inlaid into sporting gloves (such as goalkeeper's gloves) as a reinforce, to withstand the impact when hands catch a football, to prevent injuries to the fingers; alternatively, the above joint protection device can also be applied as an internal layer of surface decorative parts of artificial limbs, as a support of the decorative parts; through the joint protection device, the structures of the artificial limbs can be simplified, making it more aesthetic, while keeping it flexible.

Based on the above technical features, the joint protection device proposed in the embodiments of the invention can be firmly attached to a joint part, does not affect the normal joint movement, and effectively protect joints; moreover, it is simple in structure and low in cost, and can be efficiently and conveniently worn and detached.

The joint protection device according to the present disclosure also comprises a footwear. The joint protection body in the joint protection device can be used in combination with the footwear to play a role of ankle protection. Detailed description is given below in combination with the figures and embodiments.

Referring to FIGS. 20-34, an embodiment of the present disclosure provides a footwear 4 capable of being used in combination with the joint protection body to play a role of ankle joint protection. The footwear 4 comprises a shoe sole 31, an upper 32 and a heelpiece 30. The joint protection body 1 mentioned above is disposed at the heelpiece 30. The longitudinal and transverse shapes of the joint protection body 1 are kept consistent with the shape of the wearer's foot. The joint protection body 1 is an integrally formed rigid hollow housing which opens at the bottom and the leg part, and comprises a front supporting portion and side supporting portions distributed on two sides of the front supporting portion. The front and side supporting portions wrap respectively around the front and sides of the ankle joint to provide front and side support for the ankle joint. The joint protection body 1 is provided with at least one notch 10 in a portion corresponding to the wearer's ankle. The notch 10 divides the joint protection body 1 into a plurality of joint pieces which are segmented, wherein, the upper segments of the joint pieces 12 are leg supporting members 38, the lower segments of the joint pieces 12 are foot fixing members 36, and the middle segments of the joint pieces 12 are intermediate connecting members 37. Adjacent joint pieces 12 are connected by two local junctions 13 respectively provided at appropriate positions on two sides of the joint protection body 1. Adjacent joint pieces 12 are capable of rotating with the local junctions 13 serving as rotation fulcrums, thereby ensuring that the ankle can move freely. Adjacent joint pieces 12 contact each other and stop rotating when the joint pieces 12 rotate about the rotation fulcrums to a limiting position.

Optionally, in an embodiment of the present disclosure, the heights of the adjacent joint pieces 12 increase or decrease in a step-wise manner. The joint protection body 1 is placed laterally of, behind, and medially of a heel of the wearer's foot, and in a state in which the human's leg is upright, the longitudinal axis X1 of the joint protection body 1 is consistent with the longitudinal axis X2 of the heelpiece 30. The lower part of the joint protection body 1 is at least partially fixed to the heelpiece 30, while the area, corresponding to the rear of the heel, of the joint protection body 1 is not fixed to the heelpiece 30. The contour of the joint protection body 1 is designed to be consistent with the contour of the shoe sole 31 in the portion close to the shoe sole 31, but gradually expands laterally in an upward direction. The joint protection body 1 is higher than the ankle and wraps around the rear and two sides of the wearer's foot and leg. A cushion structure 34 is provided between the joint protection body 1 and the wearer's foot. A fastener 33 of the footwear 4 fits and fixes the joint protection body 1 to the wearer's foot and leg.

Optionally, the heights of the plurality of joint pieces 12 increase or decrease in a step-wise manner. When the joint bends, adjacent joint pieces overlap without interfering with each other or affecting joint movements, thereby ensuring that the joint can move freely, and other structures on the footwear 4 can be prevented from getting stuck in the notch. In addition, in terms of the supporting effect, the increase or decrease of the heights of the adjacent joint pieces 12 in a step-wise manner can avoid the problems of influence to the rigidity and supporting performance of the whole joint protection device due to the needs to enlarge and widen the notch and to reduce the width of each joint connecting member in order to prevent mutual interference between the joint pieces 12 when the joint is moving. The lower part of the joint protection body 1 is at least partially fixed to the heelpiece 30, and this fixation includes a direct or indirect fixation to the heelpiece 30 and its adjacent positions. The fixation manner may be one or a combination of the conventional fixation manners such as glue fixation and a suturing fixation, and may also be other possible fixation manners, such as sewing the inner and outer layers of the upper vamp in areas corresponding to the joint protection body 1 into a closed region, and wrapping the joint protection body 1 inside the closed region. The area, corresponding to the rear of the foot sole, of the joint protection body 1 is not fixed to the heelpiece 30, ensuring that the joint protection body 1 and the inner and outer layers of the heelpiece 30 can slide relative to each other at this position, thereby ensuring the flexibility of the footwear 4. The cushion structure 14 can be made of sponge or other soft materials. The contour of the joint protection body 1 is designed to be consistent with the contour of the shoe sole 31 in the portion close to the shoe sole 31, but gradually expands laterally in an upward direction, so as to allow enough space for filling of more cushion material for body parts that have higher cushioning requirements and are relatively fragile (such as an ankle and an inner side of a leg), without affecting the accommodation of the wearer's leg and foot. The fastener 33 of the shoe includes a direct tying structure (such as a shoelace, a strap, etc.), and further includes an indirect tying structure (such as an upper, a shoe buckle, a shoelace hole, etc.) connected with the direct tying structure. In conclusion, the combined use of the joint protection body 1 with the footwear 4 in the present disclosure not only can effectively protect the ankle without affecting foot movements, but also can effectively ensure that the shoe bends correspondingly with the wearer's movement to ensure flexibility of the shoe when worn.

Figure 22:
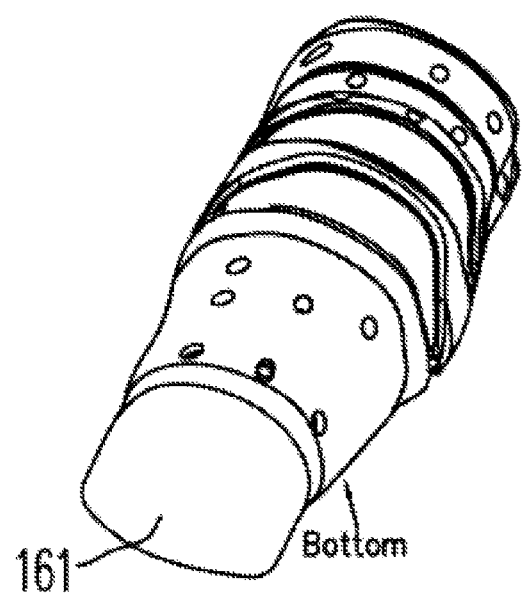
FIG. 22 is a structural diagram of the joint protection body in FIG. 20, which extends to a shoe sole.
Figure 23:
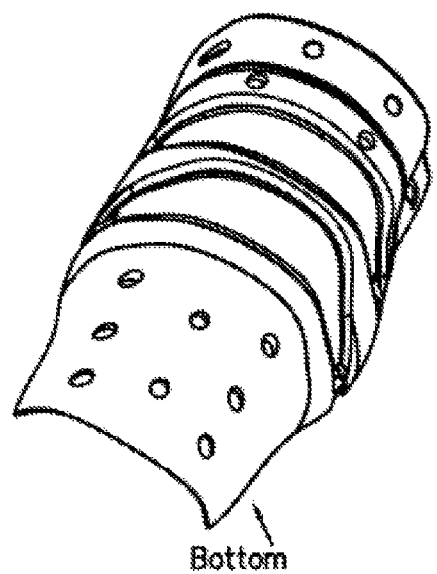
FIG. 23 is a structural diagram of the joint protection body in FIG. 20 with a completely opened bottom.
Figure 24:
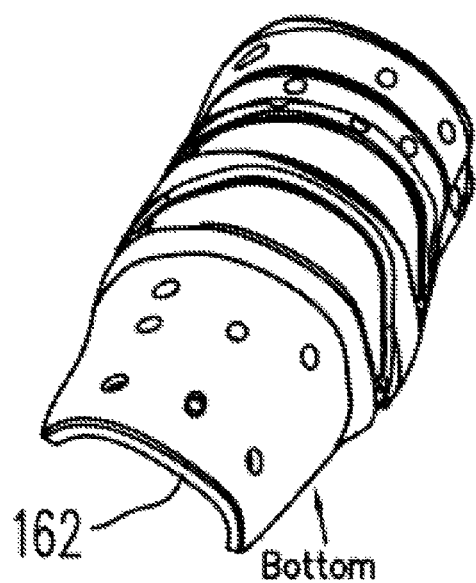
FIG. 24 is a structural diagram of the joint protection body in FIG. 20 with a sutured fixing portion extending at the bottom end.

Referring to FIG. 22, in an embodiment of the present disclosure, the bottom end of the joint protection body 1 extends in a direction of the shoe sole 31 to form a foot sole supporting member 161 which can be fixedly connected to the shoe sole 31. Alternatively, the end, close to the foot sole, of the joint protection body 1 can only extend in a lateral direction of the heelpiece 30, and is completely opened in a direction of the shoe sole 31, as shown in FIG. 23. When it is completely opened, the bottom edge of the joint protection body 1 is not fixed to the shoe sole 31. Alternatively, although the end, close to the foot sole, of the joint protection body 1 opens in the direction of the shoe sole 31, the bottom edge of the joint protection body 1 has a fixing structure 162 that fixes the joint protection body 1 to the shoe sole 31, as shown in FIG. 24. The two solutions illustrated by in FIGS. 23 and 24 produce no feeling of hard objects on the foot sole, thus will not influence the comfort level and proprioception of the foot sole, and thereby can ensure the comfort level of the wearer when wearing it.

Figure 20:
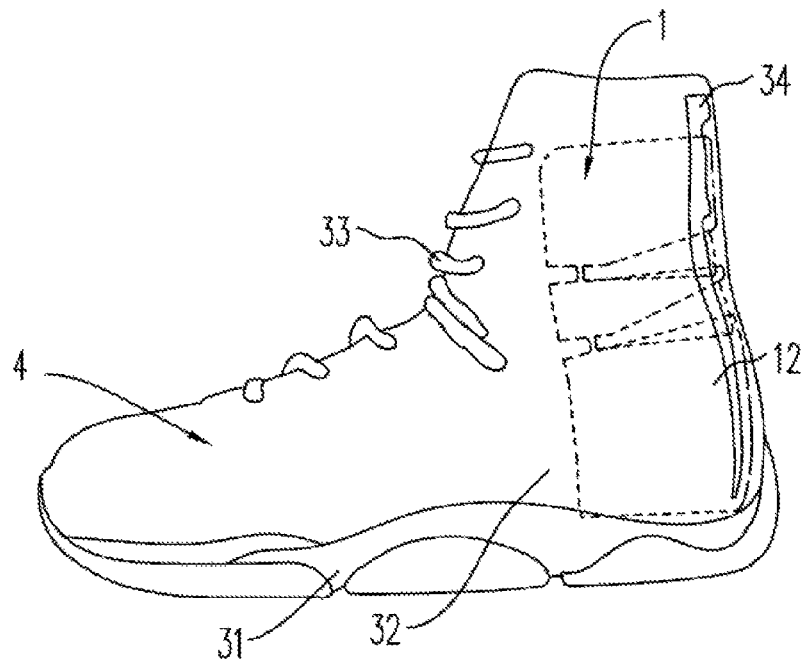
FIG. 20 is a structural diagram of a footwear used in combination with a joint protection body according to the present disclosure.
Figure 21:
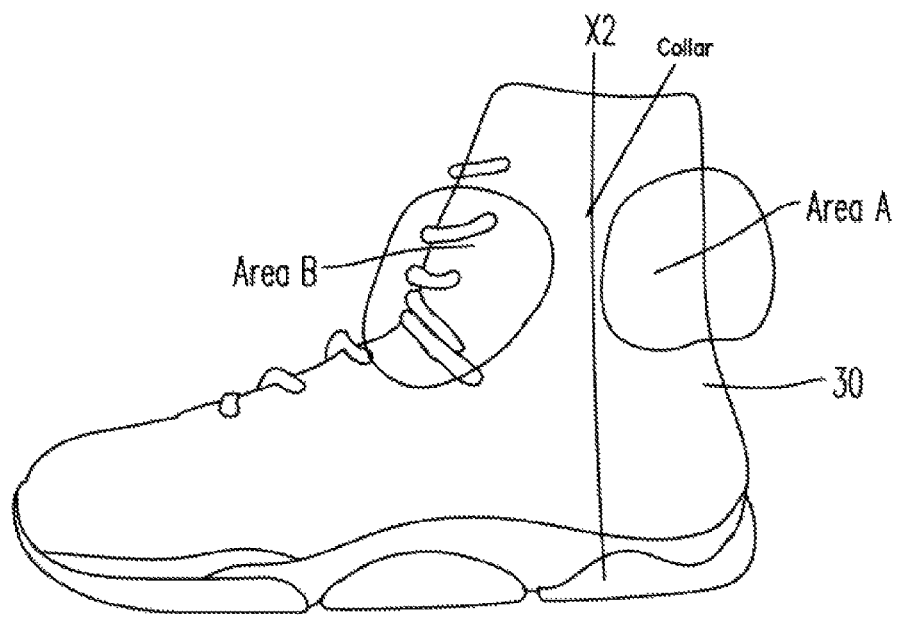
FIG. 21 is a structural diagram of a footwear that is not used in combination with a joint protection body according to the present disclosure.

Further, referring to FIG. 20, the joint protection body 1 is placed and fixed between the inner and outer layers of the upper 32. Of course, for the appearance or other reasons, the upper 32 may also be provided with a local opening to expose the joint protection body 1. In order that the movement performance of the joint protection body 1 for an ankle can be fully exerted, the inner and outer layers of the front and rear areas (i.e. "Area A" and "Area B") of the collar corresponding to the ankle are made of an elastic material, so that the inner and outer layers are elastic in a direction from the heel to the leg (i.e. a longitudinal direction).

Further, referring to FIGS. 20 and 32-34, if the general cushion material (e.g. sponge) in the shoe does not have a good elasticity, a certain limitation will exist when applying the cushion material to the ankle protecting shoe according to the present disclosure, which affects the flexibility of the shoe in use. In addition, the strength of sponge is not high, and different positions of the foot have different requirements for cushioning, for example, the requirement for cushioning under the heel is relatively low, hence the sponge under the heel can be very thin; and in contrast, the requirement for cushioning at the ankle joints on both sides is relatively high, hence the sponge at the ankle joints on both sides needs to be thicker. However, the sponge is usually a thin sheet of uniform thickness, and it is difficult to cut it into nonuniformity thicknesses. Therefore, the cushion structure 34 in the ankle protecting shoe according to the present disclosure is preferably formed by adhering a foam member 5, which has been molded using a mold, to the joint protection body 1.

Further, in order to improve the quality and efficiency, a process of foam injection molding may also be employed. A high-strength foam material is directly molded onto the joint protection body to fabricate a joint protection body 6 with foam=inside it. The hardness of the foam material is very important for the performance of the footwear 4. If the foam material is too hard, it will affect the comfort level of the shoe. If it is too soft, the thickness of the foam member 5 must be increased, and if the material is too soft, its strength will also decrease. Therefore, the foam member 5 preferably has a hardness between 13 HC and 30 HC. The foam with a hardness within this range has the best overall performance and can ensure the comfort level of the wearer.

Figure 25:
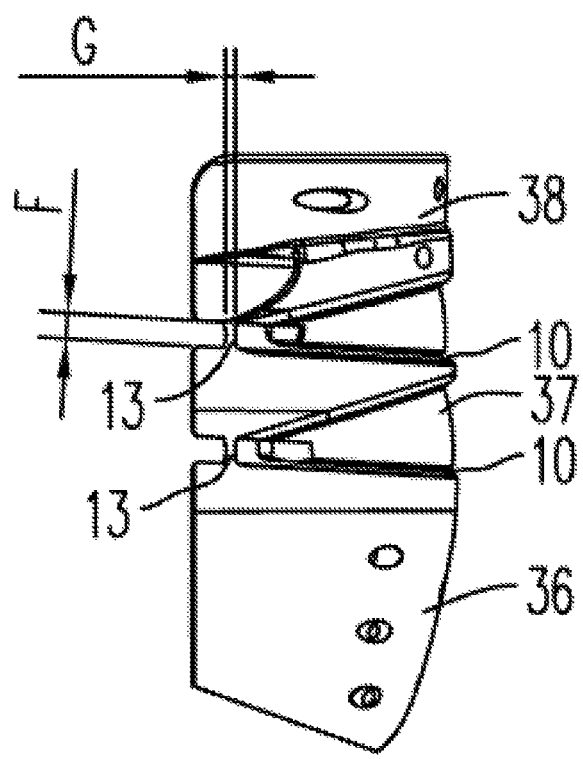
FIG. 25 is a side view of the joint protection body in FIG. 20.
Figure 26:
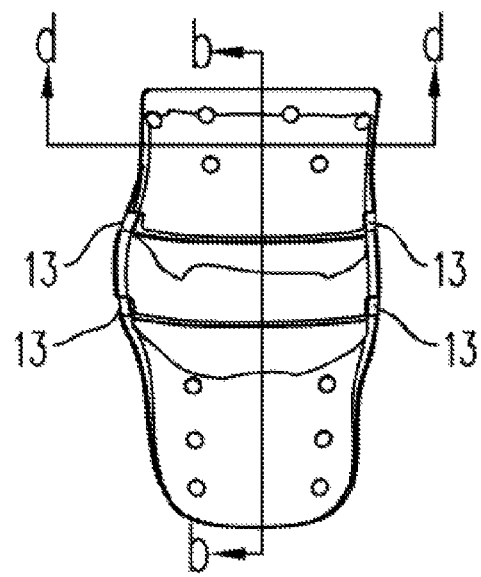
FIG. 26 is a front view of the joint protection body in FIG. 20.
Figure 27:
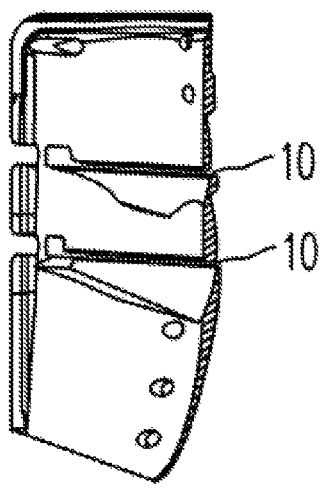
FIG. 27 is a longitudinal b-b section view of the joint protection body in FIG. 26.
Figure 28:
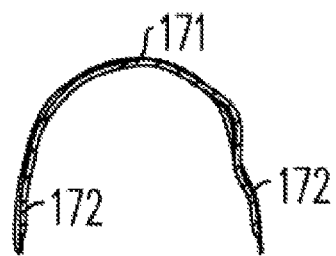
FIG. 28 is a lateral d-d section view of the joint protection body in FIG. 26.
Figure 29:
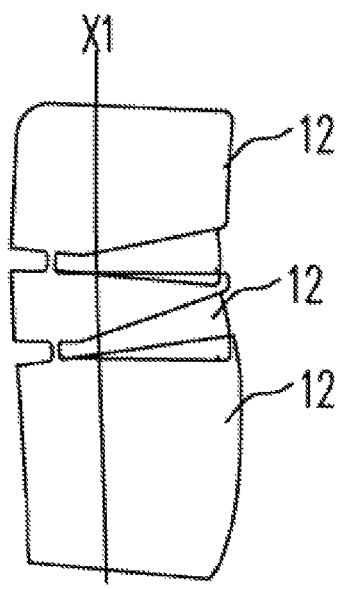
FIG. 29 is a diagram of a joint protection body when the leg is in an upright standing state.

Since shoes are products that are worn on feet for a long time, the life span of the shoes is very important. For the footwear 4 in the present disclosure, the weakest portions are the local junctions 13 between adjacent joint pieces, i.e. the rotation fulcrums between the adjacent joint pieces. Referring to FIG. 25, in an embodiment of the present disclosure, a ratio G:F of the minimum thickness G to the length F of the local junction 13 is between 0.15 to 1.1. Within this range, the comprehensive properties such as strength, rigid and service life of the joint protection device are good, which allow the joint protection device to be bent easily on the premise of ensuring its rigidity and strength, thereby ensuring the flexibility of the ankle protecting shoe. If G:F is less than 0.15, the rigidity of the joint protection body 1 used for an ankle is too poor, and hence the ankle protecting effect of the shoe is reduced. Meanwhile, the local junctions 13 does not have enough tensile strength and is prone to breakage. If G:F is greater than 1.1, the local junction 13 has a poor fatigue strength, thus the joint protection body 1 used for an ankle is difficult to bend, which affects the flexibility of the shoe.

Further, in order to ensure that each joint piece 12 produces as little lateral offset as possible when rotating, which affects the flexibility of the joint, each lateral notch 10, 15 is approximately horizontal, and the angle between each lateral notch 10, 15 and a horizontal direction is within ±35°. In this range, the joint protection device has a small radial offset during joint movement, thereby ensuring the comfort level and flexibility of the ankle protecting shoe.

Figure 30:
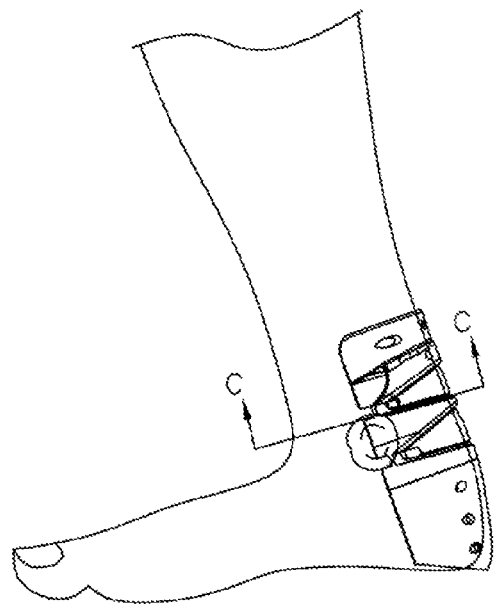
FIG. 30 is a diagram of a joint protection body disposed on the foot.
Figure 31:
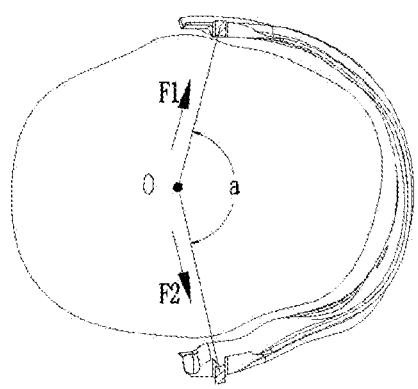
FIG. 31 is a lateral c-c section view of the joint protection body in FIG. 30.
Figure 32:
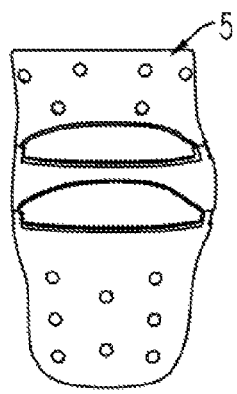
FIG. 32 is a diagram of a foam member shaped by molding.
Figure 33:
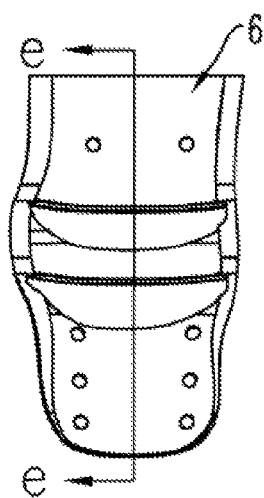
FIG. 33 is a rear view of a joint protection body with foam adhered thereto or infusion molded therein.
Figure 34:
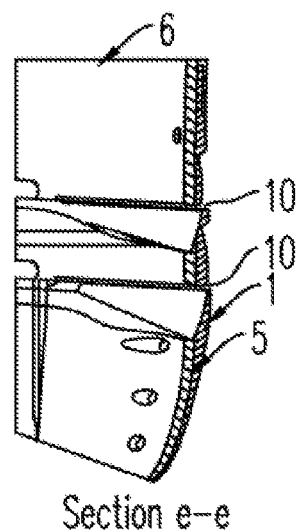
FIG. 34 is a longitudinal e-e section view of the joint protection body in FIG. 33.

In an embodiment of the present disclosure, referring to FIGS. 30 and 31, which illustrate the structure and force-bearing status of a cross-section c-c corresponding to a notch, and the direction from the local junctions 13 on two sides of the joint protector body 1 to an ankle center is a direction in which the joint protection device provides support for the ankle. The included angle a formed between the ankle center O and the two local junctions 13 on two sides of the joint protection body 1 matters to the supporting effect of the joint protection body 1 for the ankle. In this embodiment, on a cross section of the joint protection body 1, the included angle a between the ankle center O and the connecting line between the two local junctions 13 is a>80°, and thus, the joint protection device including the joint protection body 1 has a better lateral support effect for the ankle; when a=180°, the line between the ankle center O and the two local junctions 13 on two sides of the joint protection body 1 are on the same straight line, and hence the joint protection device has the best lateral support effect for the ankle; and when a<80°, the joint protection device has a weaker lateral support effect for the ankle and cannot effectively protect the ankle.

The above-mentioned footwear 4 includes various shoes that need the ankle protection function (for example, roller skates, basketball shoes, football shoes, badminton shoes, outdoor sports shoes, etc.). Since their structures and functions are basically the same, they will not be specifically described and defined here.

In addition, the above are merely specific implementations of the present disclosure, but the protection scope of the present disclosure is not limited to this. The skilled familiar to the art can make various equivalent transformations and substitutions without departing from the spirit of the invention and these transformations and substitutions fall within the scope defined by claims.

What is claimed is:

1. A joint protection device, comprising a joint protection body whose longitudinal and horizontal shapes match a shape of a joint, the joint protection body being an integrally formed rigid hollow housing with an opened bottom and comprising a front supporting portion and side supporting portions distributed on two sides of the front supporting portion; at least one notch being provided in an area, close to a joint movement, of the joint protection body, the at least one notch dividing the joint protection body into a plurality of joint pieces, adjacent joint pieces being connected by two local junctions respectively provided at appropriate positions on two sides of the joint protection body, the adjacent joint pieces being capable of rotating with the local junctions as rotation fulcrums; and when the joint pieces rotate around the rotation fulcrums to a limiting position, the adjacent joint pieces contacting with each other and stopping rotating.

2. The joint protection device according to claim 1, wherein heights of the plurality of joint pieces increase or decrease in a step-wise manner.

3. The joint protection device according to claim 2, wherein one end of the joint protection body extends to form a thin wall having an L-shape in a cross section.

4. The joint protection device according to claim 1, wherein the joint protection device further comprises a strip-shaped fixing belt, one end of the fixing belt is integrally formed on one side of the joint protection body while the other end of the fixing belt is provided with at least one buckle, the joint protection body is provided with through holes matched with the buckle, and the fixing belt is configured to be wrapped around the joint and fastened to the through holes by means of the buckle;

wherein the other end of the fixing belt is further provided with at least one saw-toothed barb, and the joint protection body is further provided with corresponding through holes or semi-through holes matched with the saw-toothed barb.

5. The joint protection device according to claim 1, wherein the joint protection device further comprises at least one of an opened fixing ring and a closed fixing ring which are fixed to the joint protection body.

6. The joint protection device according to claim 1, wherein an elastomer with a good elasticity is injected between the joint pieces through overmolding, to support a part of a body weight by an elasticity of the elastomer when the joint protection body is bent.

7. The joint protection device according to claim 1, wherein at least one joint piece is further provided with hook-shaped structures that are mutually cooperated, and when the joint is bent inwardly until the hook-shaped structures contact with each other, the joint stops bending; wherein the joint protection body is further provided with a notch, a middle part of the notch is provided with a junction, and the joint pieces on two sides of the junction rotate in any direction with the junction as a rotation fulcrum.

8. The joint protection device according to claim 1, wherein the joint protection device further comprises a footwear, the joint protection body is provided within the footwear, the footwear comprises a shoe sole, an upper and a heelpiece, and the joint protection body is disposed at the heelpiece.

9. The joint protection device according to claim 8, wherein,
- heights of the adjacent joint pieces increase or decrease in a step-wise manner;
- the joint protection body is configured to be placed laterally of, behind, and medially of a heel of a wearer's foot, and in a state in which the wearer's leg is upright, a longitudinal axis (X1) of the joint protection body is consistent with a longitudinal axis (X2) of the heelpiece;
- a lower part of the joint protection body is fixed to the heelpiece, and an area, corresponding to the rear of the heel, of the joint protection body is not fixed to the heelpiece;
- a cushion structure is configured to be provided between the joint protection body and the wearer's foot;
- a contour of a bottom edge of the joint protection body is designed to be consistent with a contour of the shoe sole at its bottom edge, but gradually expands laterally in an upward direction; and
- a fastener of the footwear is configured to fit and fix the joint protection body to the wearer's leg and foot.

10. The joint protection device according to claim 9, wherein the cushion structure is configured to be positioned between the joint protection body and the wearer's foot is formed by one of the following:
- adhering a foam member, which is foam molded by using a mold, to the joint protection main body; and
- directly molding a foam material onto the joint protection body by using a mold.

11. The joint protection device according to claim 10, wherein a hardness of the foam member is between 13 HC and 30 HC.

12. The joint protection device according to claim 8, wherein,
- an end, close to a foot sole, of the joint protection body extends in a lateral direction of the heelpiece, and is completely opened in a direction of the shoe sole; or
- the end, close to the foot sole, of the joint protection body opens in the direction of the shoe sole, while a bottom edge of the joint protection body has a fixing structure that fixes the joint protection body to the shoe sole;
- wherein the joint protection body is placed and fixed between inner and outer layers of the upper; the inner and outer layers of front and rear areas, corresponding to an ankle during use, of a collar of the footwear are elastic in a direction from the heel to the leg during use.

13. The joint protection device according to claim 8, wherein a ratio G: F of a minimum thickness G to a length F of the local junction is between 0.15 and 1.1;
- and an included angle formed between the notch and a horizontal direction is within ±35°.

\* \* \* \* \*